US011883815B2

(12) United States Patent
Mumm

(10) Patent No.: US 11,883,815 B2
(45) Date of Patent: Jan. 30, 2024

(54) APPARATUS FOR STERILE TRANSFER OF MATERIAL BETWEEN A CONTAINER AND AN ISOLATOR

(71) Applicant: ATEC PHARMATECHNIK GMBH, Soerup (DE)

(72) Inventor: Hans-Werner Mumm, Soerup (DE)

(73) Assignee: ATEC PHARMATECHNIK GMBH, Soerup (DE)

( * ) Notice: Subject to any disclaimer, the term of this patent is extended or adjusted under 35 U.S.C. 154(b) by 279 days.

(21) Appl. No.: 17/609,412

(22) PCT Filed: Apr. 9, 2020

(86) PCT No.: PCT/EP2020/060234
§ 371 (c)(1),
(2) Date: Nov. 8, 2021

(87) PCT Pub. No.: WO2020/229067
PCT Pub. Date: Nov. 19, 2020

(65) Prior Publication Data
US 2022/0250050 A1    Aug. 11, 2022

(30) Foreign Application Priority Data
May 10, 2019    (DE) .................... 10 2019 003 317 .5

(51) Int. Cl.
*B01L 1/02*          (2006.01)
*B01L 3/00*          (2006.01)
(Continued)

(52) U.S. Cl.
CPC ............. *B01L 1/02* (2013.01); *B01L 3/50825* (2013.01); *B65D 45/345* (2013.01); *F16J 13/24* (2013.01);
(Continued)

(58) Field of Classification Search
CPC .. B01L 1/02; B01L 3/50825; B01L 2200/026; B01L 2200/141; B01L 2300/04; B65D 45/345; F16J 13/24
See application file for complete search history.

(56) References Cited

U.S. PATENT DOCUMENTS 4,494,586 A  *  1/1985 Picard .................... G21F 7/005
                                                         976/DIG. 356
5,421,626 A     6/1995 Glachet
(Continued)

FOREIGN PATENT DOCUMENTS

DE    693 07 433 T2    7/1997
FR    2 695 343 A1     3/1994
(Continued)

*Primary Examiner* — Timothy L Maust
(74) *Attorney, Agent, or Firm* — Norman B. Thot

(57) ABSTRACT

An apparatus for a sterile transfer of a material incudes a second safety device which locks an actuation mechanism in a closed position and unlocks the actuation mechanism when a container flange is correctly connected to a port flange, a third safety device which locks the container flange connected to the port flange when the actuation mechanism leaves the closed position, and a fourth safety device which blocks a return of the actuation mechanism from the open position to the closed position when the port door is open. The second, third and/or fourth safety device comprises two magnetic elements with at least one closed wall being arranged between the two magnetic elements. The two magnetic elements are configured to mutually attract or to mutually repel through the at least one closed wall either in a lock position or in an unlock position of the second, third and/or fourth safety device.

14 Claims, 10 Drawing Sheets

(51) Int. Cl.
 *B65D 45/34* (2006.01)
 *F16J 13/24* (2006.01)
(52) U.S. Cl.
 CPC ... *B01L 2200/026* (2013.01); *B01L 2200/141* (2013.01); *B01L 2300/04* (2013.01)

(56) References Cited

U.S. PATENT DOCUMENTS

| | | | |
|---|---|---|---|
| 5,425,400 | A | 6/1995 | Szatmary |
| 5,853,207 | A * | 12/1998 | Saint Martin ............. B01L 1/02 292/257 |
| 6,315,013 | B1 | 11/2001 | Lardieri |
| 8,919,830 | B2 * | 12/2014 | Norton ...................... B01L 1/02 414/217 |
| 9,704,607 | B2 * | 7/2017 | Chavrot .................. G21F 7/005 |
| 10,748,669 | B2 * | 8/2020 | Dufour .................... G21F 7/005 |
| 11,684,913 | B2 * | 6/2023 | Yi .......................... A61J 1/2093 292/257 |
| 2003/0126799 | A1 | 7/2003 | Porret et al. |
| 2012/0153610 | A1 * | 6/2012 | Young .................... G21F 7/005 285/335 |
| 2014/0291995 | A1 | 10/2014 | Chavrot |
| 2016/0201382 | A1 | 7/2016 | Dufour et al. |
| 2016/0354772 | A1 | 12/2016 | Nodin |
| 2022/0250050 | A1 * | 8/2022 | Mumm ................ B65D 45/345 |

FOREIGN PATENT DOCUMENTS

| | | |
|---|---|---|
| WO | WO 2013/053844 A1 | 4/2013 |
| WO | WO 2015/032713 A1 | 3/2015 |

* cited by examiner

APPARATUS FOR STERILE TRANSFER OF MATERIAL BETWEEN A CONTAINER AND AN ISOLATOR

CROSS REFERENCE TO PRIOR APPLICATIONS

This application is a U.S. National Phase application under 35 U.S.C. § 371 of International Application No. PCT/EP2020/060234, filed on Apr. 9, 2020 and which claims benefit to German Patent Application No. 10 2019 003 317.5, filed on May 10, 2019. The International Application was published in German on Nov. 19, 2020 as WO 2020/229067 A1 under PCT Article 21(2).

FIELD

The present invention relates to an apparatus for the sterile transfer of material between a container and an isolator.

BACKGROUND

Apparatuses of this type are also known as rapid transfer ports. Rapid transfer ports comprise an alpha part in the wall of the isolator, consisting substantially of the port flange and the port door, and a beta part consisting substantially of the container flange and the container cover, which is docked to the alpha part before the transfer of material. A rapid transfer port of this type is described, for example, in U.S. Pat. No. 9,704,607 B2 and in WO 2013/053844 A1. This apparatus possesses a total of five safety devices in the form of bolts, which prevent an accidental contamination of the material from occurring through unintentional contact with the environment while material is being transferred from the container into the isolator or while material is being transferred from the isolator into the container, or conversely prevent that toxic substances from the container and/or isolator can enter the environment, for example, as a result of improper operation of the apparatus, which is intended to be prevented with the aid of the safety devices.

Similar apparatuses of this type with a smaller number of safety devices are described in FR 2 695 343 A1 or in WO 2015/032713 A1.

The first safety device prevents the port door from being opened if the container is not provided with a container cover. If the port door is closed and abuts against the container cover, the bolt is in its unlock position, in which the actuation mechanism can be brought into the open position. If the closed port door does not abut against a container cover, the bolt is in its lock position, in which it prevents the actuation mechanism from being brought into the open position.

The second safety device prevents the port door from being opened as long as the container flange is not correctly connected to the port flange, i.e., is not properly docked to the port flange. The bolt in its lock position in this case locks the actuation mechanism in the closed position so that it can only leave the closed position and head towards the open position if the flanges of the container and of the isolator are properly connected to each other. A bayonet connection is usually employed to connect the two flanges, which is correctly made if a lug of the container flange abuts against a shoulder of the port flange.

The third safety device prevents the two flanges from being released from one another as long as the port door is open, i.e., while the actuation mechanism is in its open position or between its closed position and its open position. The bolt in its lock position in this case prevents a rotation of the two flanges, which could lead to a release of the bayonet connection. When the actuation mechanism is in its closed position, the bolt is in its unlock position, in which it allows the rotation of the two flanges and the release of the bayonet connection.

The fourth safety device serves to prevent a release of the container flange from the port flange after the actuation mechanism has been moved to the open position and the port door has been opened together with the container cover connected to the port door. The bolt in the lock position in this case prevents the actuation mechanism from returning to its closed position when it is in its open position or between its closed position and its open position. When the actuation mechanism is in its closed position, the bolt is in its unlock position.

The fifth safety device described in detail in U.S. Pat. No. 9,704,607 B2 and WO 2013/053844 A1 is needed only very rarely, and specifically only in the case of deliberate improper operation or a complete lack of familiarity with the operating principle of the apparatus on the part of the operator. The bolt locks the actuation mechanism in this case if the container flange is not properly connected to the port flange between the unlocking of the actuation mechanism by the second safety device and the locking of the container flange by the third safety device.

In the apparatus from U.S. Pat. No. 9,704,607 B2 and WO 2013/053844 A1, the bolt of the first safety device is inserted in an axially movable manner into a through-hole of the port door, while the bolt of the third safety device and parts of the bolts of the second and fifth safety devices are inserted in an axially movable manner into a through-hole of the port flange. The bolts have diameters of a few millimeters.

When apparatuses of this type are employed in the pharmaceutical or medical sector, where complete sterility of the material inside the isolator and the container is required, the alpha part of the rapid transfer port forms a sterile barrier which must not be penetrated by either particles or germs. Since the through-holes penetrate the sterile barrier, however, seals must be inserted into the through-hole, which are intended to prevent germs from passing through the through-holes. Since the bolts move back and forth in the through-holes and, in an end position, protrude out of the holes with their free ends, particles or germs can still, however, pass through the through-holes despite the seals. The seals are also dynamically stressed by the movable bolts and can thus fail more quickly. It is also difficult to monitor the integrity of the seals, so that in the event of a seal failure there is an even greater risk of contamination. The sterilizing of the apparatus is also made more difficult since germs that have penetrated into the through-holes can only be killed incompletely or not at all, and thus can likewise lead to contamination.

SUMMARY

An aspect of the present invention is to improve an apparatus of the type mentioned above so that, in the region of the safety devices, the risk of possible contamination of the isolator or of the container can be reduced and if possible, prevented.

In an embodiment, the present invention provides an apparatus for a sterile transfer of a material between a container and an isolator. The container comprises a container opening, a container flange which is configured to surround the container opening, and a container cover which is configured to close off the container opening and to be removable from the container flange. The isolator comprises a port opening, a port flange which is configured to surround the port opening, a port door which is configured to close off the port opening, and an actuation mechanism which is configured to move between a closed position and an open position so as to open and close the port door. The container flange is configured to be releasably connected to the port flange. The container cover is configured to be releasably connected to the port door. The apparatus further comprises at least one of a first safety device which is configured to lock the actuation mechanism in the closed position and to unlock the actuation mechanism when the port door abuts against the container cover, a second safety device which is configured to lock the actuation mechanism in the closed position and unlock the actuation mechanism when the container flange is correctly connected to the port flange, a third safety device which is configured to lock the container flange connected to the port flange when the actuation mechanism leaves the closed position, a fourth safety device which is configured to block a return of the actuation mechanism from the open position to the closed position when the port door is open, and a fifth safety device which is configured to lock the actuation mechanism if the container flange is not correctly connected to the port flange between the unlocking of the actuation mechanism by the second safety device and the locking of the container flange by the third safety device. At least one of the second safety device, the third safety device, and the fourth safety device comprises two magnetic elements which are configured to be movable relative to each another. At least one closed wall without a through-opening is arranged between the two magnetic elements. The two magnetic elements are configured to mutually attract or to mutually repel through the at least one closed wall either in a lock position or in an unlock position of the at least one of the second safety device, the third safety device and the fourth safety device, as the case might be.

BRIEF DESCRIPTION OF THE DRAWINGS

The present invention is described in greater detail below on the basis of embodiments and of the drawings in which.

DETAILED DESCRIPTION

Figure 1:
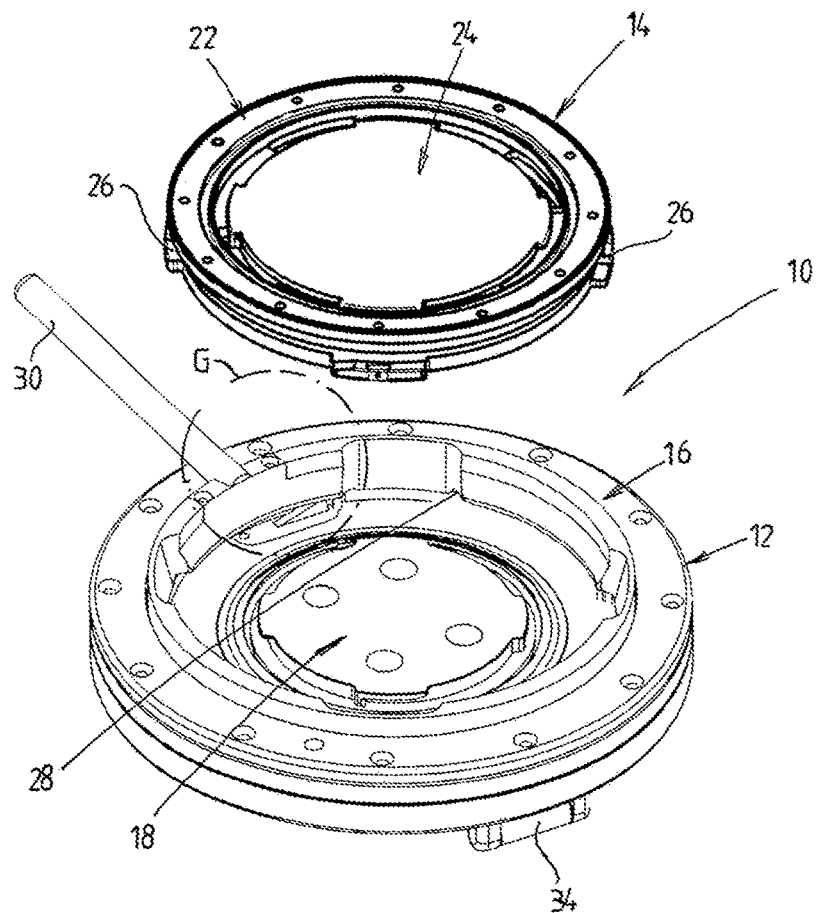
FIG. 1 is a perspective view of a port flange and a port door of an apparatus according to the present invention before the docking of a container, of which only the container flange and the container cover are illustrated.
Figure 2:
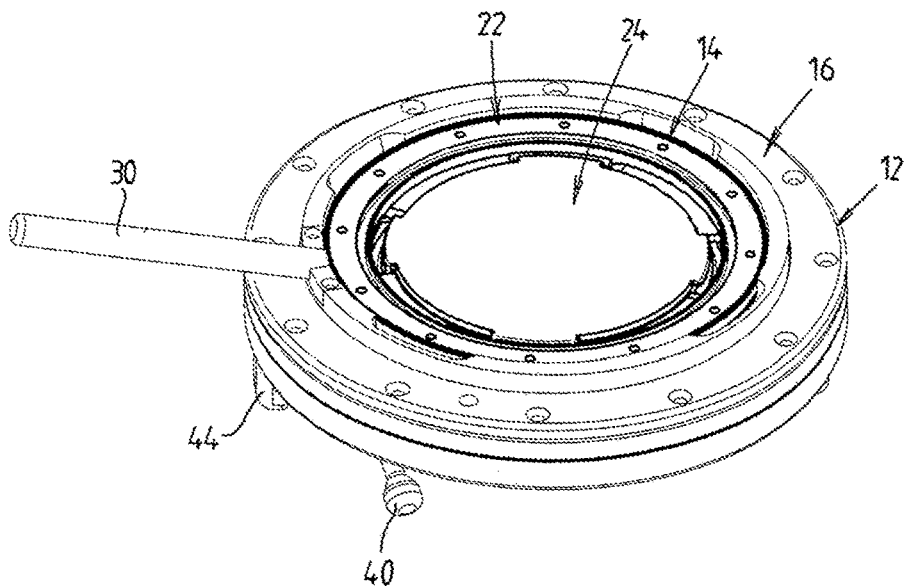
FIG. 2 is a perspective view corresponding to FIG. 1, but after the docking of the container.

The present invention provides at least one and, for example, more than one of the safety devices, which each comprise two magnetic elements that are movable relative to one another, at least one closed wall without a through-opening which is arranged between the two magnetic elements, and that the magnetic elements mutually attract or repel through the closed wall in either a lock position or an unlock position of the safety device.

Since the at least one closed wall without a through-opening between the two magnetic elements is impenetrable by germs, penetration of the sterile barrier can be reliably prevented, in contrast to known safety devices. The safety devices according to the present invention can be activated, i.e., brought from their lock position to their unlock position and vice versa, in a contactless manner through the at least one closed wall between the two magnetic elements. One of the two magnetic elements is in each case here brought so close to the other magnetic element that the magnetic attractive or repulsive forces acting between the two magnetic elements through the wall cause a movement of the other magnetic element, the effect of which is that the safety device assumes the lock position or the unlock position.

It is in principle sufficient if a single closed wall is arranged between the two magnetic elements. Since the two magnetic elements are always arranged in different components of the apparatus, which are movable relative to one another, e.g., one in the port flange and the other in the actuation mechanism, or one in the port door or a component that is movable together with the port door and the other in the port flange, two closed walls can, for example, be arranged between the magnetic elements, which tightly seal each of the two components against the inside of the isolator.

It is in principle possible to equip the apparatus with only one of the five safety devices, e.g., with the third safety device, which prevents the container from being detached from the isolator as long as the port door is open. This safety device is in this case equipped with two magnetic elements.

It is furthermore also possible, however, to equip the apparatus with two, three or four safety devices, such as, for example, the apparatus described in FR 2 695 343 A1. A single one or a plurality of the safety devices can in this case be equipped with two magnetic elements. Those safety devices in which a through-hole would otherwise be necessary in one of the components can, for example, always be equipped with two magnetic elements.

Safety devices according to the present invention can be employed irrespective of the construction of the apparatus or of the rapid transfer port; there are, for example, rapid transfer ports where the actuation mechanism or a rotatable lock part of a lock thereof is attached to the inside of the port flange, as described, for example, in U.S. Pat. No. 9,704,607 B2. There are alternatively rapid transfer ports where the actuation mechanism or a rotatable lock part of a lock thereof is movable together with the port door, as described below.

Safety devices according to the present invention can also be employed not only in rapid transfer ports in which the opening and closing of the port door and the operation of the actuation mechanism take place manually, e.g., via a glove protruding into the inside of the isolator, but also in rapid transfer ports in which the opening and closing of the port door and the operation of the actuation mechanism take place with the aid of motorized drives, e.g., from the outside of the isolator.

An advantageous embodiment of the present invention provides that each of the two magnetic elements of a safety device can, for example, comprise a permanent-magnetic body. This embodiment has the advantage that it is possible to work with either attractive or repulsive forces between the two magnetic elements, as desired. If it is intended to work only with attractive forces between the two magnetic elements, however, it is alternatively also possible to provide one of the two magnetic elements with a ferromagnetic body and the other with a permanent-magnetic body. It would also in principle be possible for at least one of the magnetic elements to be in the form of an electromagnet, although this would require a power supply.

There are, in principle, four alternatives for the operating principle of the magnetic elements of a particular safety device:
1) The magnetic elements mutually attract in the lock position, but not in the unlock position;
2) The magnetic elements mutually repel in the lock position, but not in the unlock position;
3) The magnetic elements mutually attract in the unlock position, but not in the lock position; and
4) The magnetic elements mutually repel in the unlock position, but not in the lock position.

A further advantageous embodiment of the present invention provides that at least one of the two magnetic elements is movable within the component in which it is installed, e.g., the port flange, the port door, or the actuation mechanism, between two end positions which respectively correspond to the lock position and the unlock position of the particular safety device. It is sufficient in some cases if only one of the two magnetic elements is movable between two end positions, while it is advantageous in other cases if both magnetic elements are movable between two end positions.

Since the two magnetic elements according to the present invention are movable relative to one another, one magnetic element can be moved closer to the other magnetic element or can be moved away from it. This relative movement of the one magnetic element relative to the other magnetic element can be triggered by a movement of a component of the apparatus, for example, by a movement of the actuation mechanism between its open and closed positions, by a movement of the port door when it is being opened or closed, or by a relative movement of the container flange and the port flange when they are being connected.

Owing to the mutually attractive or repulsive forces, a movement of the one magnetic element closer to the other magnetic element results in the other magnetic element moving to its one end position in which the associated safety device is in the unlock position or the lock position. A movement away from the other magnetic element results in the attractive or repulsive forces being removed or at least diminished.

For the other magnetic element to also move to its other end position in this case, so that the associated safety device is then in the lock position or the unlock position, as appropriate, the other magnetic element can, for example, be movable against the force of a return spring, which moves the magnetic element back to the other end position after the mutual attractive or repulsive forces have been removed or diminished.

In a number of known rapid transfer ports, the actuation mechanism comprises a lock with a lock part, which is rotatable about an axis of rotation from the closed position to the open position and is usually installed inside the isolator either on the port flange or on a bar projecting radially beyond the port door and which, for manual operation of the actuation mechanism, has an actuating handle which serves to rotate the lock part and which can be grasped and actuated by an operator through a glove protruding into the isolator. It is advantageous in this case if at least one of the two magnetic elements is movable parallel to the axis of rotation of the lock part. This makes it easier, when a plurality of safety devices according to the present invention are present, to install their magnetic elements side by side in the rotatable lock part and to actuate them separately from one another. The movable magnetic element advantageously serves to block a rotation of the lock part in the lock position of a safety device and to allow a rotation of the lock part in the unlock position.

One of the two magnetic elements is advantageously arranged in the port flange in at least one safety device. This can, for example, be the fourth safety device, which comprises a first magnetic element arranged in the port flange and a second magnetic element that is movable together with the port door. The second magnetic element unlocks the actuation mechanism or the rotatable lock part in the unlock position of the safety device when the port door abuts against the port flange and the two magnetic elements mutually attract or repel. Conversely, the second magnetic element locks the actuation mechanism or the rotatable lock part when the port door is opened and, as a result of the opening movement, the two magnetic elements are moved so far apart that they no longer mutually attract or repel, or no longer do so sufficiently strongly, and therefore the return spring moves the second magnetic element to the end position in which the safety device is in the lock position.

It can, however, also be the second safety device which, in addition to a first magnetic element arranged in the port flange, likewise comprises a second magnetic element acting on the actuation device. The second magnetic element in this case unlocks the actuation mechanism or the rotatable lock part thereof when the container flange and the port flange are correctly and completely connected to each other. A catch arranged in the port flange is in this case depressed fully by a lug of the container flange. The catch in turn acts on the movable first magnetic element and presses it into the end position in which it attracts or repels the second magnetic element through the at least one wall.

A further advantageous embodiment of the present invention provides that, in at least one of the safety devices, one of the two magnetic elements can, for example, be rotatable together with the rotatable lock part about the axis of rotation thereof. This is advantageously the third safety device, which comprises a first magnetic element in the port flange and a second magnetic element in the rotatable lock part, wherein the second magnetic element moves away from the first magnetic element when the lock part rotates to the open position. The latter is then moved by the force of a return spring to its other end position in which it blocks a return rotation of the container flange that is connected to the port flange.

Instead of a lock with a rotatable lock part, the actuation mechanism could also comprise a lock with a linearly movable lock part. The second magnetic element of the third safety device would in this case advantageously be movable together with the linearly movable lock part in order to move it closer to the first magnetic element in the port flange, while the second magnetic elements of the first and second safety devices would lock and unlock the linearly movable lock part.

The present invention will be explained in greater detail below with the aid of an exemplary embodiment, which is schematically illustrated in the drawings.

The apparatus 10, which is only partially illustrated in the drawings and which is also known in the specialist field as a rapid transfer port, is used for the sterile transfer of material between a container (not illustrated) and an isolator (not illustrated). The material can, for example, be rubber or plastic stoppers for infusion bottles or vials, parts of syringes, or even liquids. For an explanation of the transfer operation, reference is here made to FIG. 1 of U.S. Pat. No. 9,704,607 B2 and the accompanying description.

For the sterile transfer of material, the apparatus 10 comprises a so-called alpha part 12 or alpha port on the side of the isolator, while on the side of the container it comprises a so-called beta part 14 or beta port. The alpha part 12 possesses a port opening, which is surrounded by a port flange 16, which is also known as an alpha flange, a port door 18 for closing off the port opening, and an actuation mechanism 20 for opening and closing the port door 18. The beta part 14 possesses a container opening, which is surrounded by a container flange 22, which is also known as a beta flange, and a container cover 24, which normally closes off the container opening and can be removed from the container flange 22. For transferring the material, the beta part 14 of the container is docked to the alpha part 12 of the isolator. This takes place using two bayonet connections, which connect the container flange 22 to the port flange 16 and the container cover 24 to the port door 18 in a sealing manner while at the same time releasing the container cover 24 from the container flange 22. One bayonet connection has lugs 26 projecting radially beyond the container flange 22, which engage with a corresponding receiving groove 28 of the port flange 16 during docking. For the complete docking of the beta part 14 to the alpha part 12, the inner part of the port flange 16 is rotated about an axis perpendicular to the plane of the port opening using a lever 30 until the lugs 26 abut against corresponding lug stops in the receiving groove 28.

In other rapid transfer ports, the docking of the beta part 14 to the alpha part 12 can also take place by a rotation of the beta part 14 relative to the alpha part 12.

The port door 18 is pivotably installed on the port flange 16 so that it can be pivoted into the inside of the isolator after the docking of the container together with the cover 24 thereof. The port door 18 is provided with a bar 32 rigidly installed on the port door 18 therefor, the bar 32 extending diametrically over the inside of the port door 18. A first end of the bar 32 projecting radially beyond the circumference of the port door 18 is pivotably hinged on the inside of the port flange 16 via a pivot joint 34.

Figure 20:
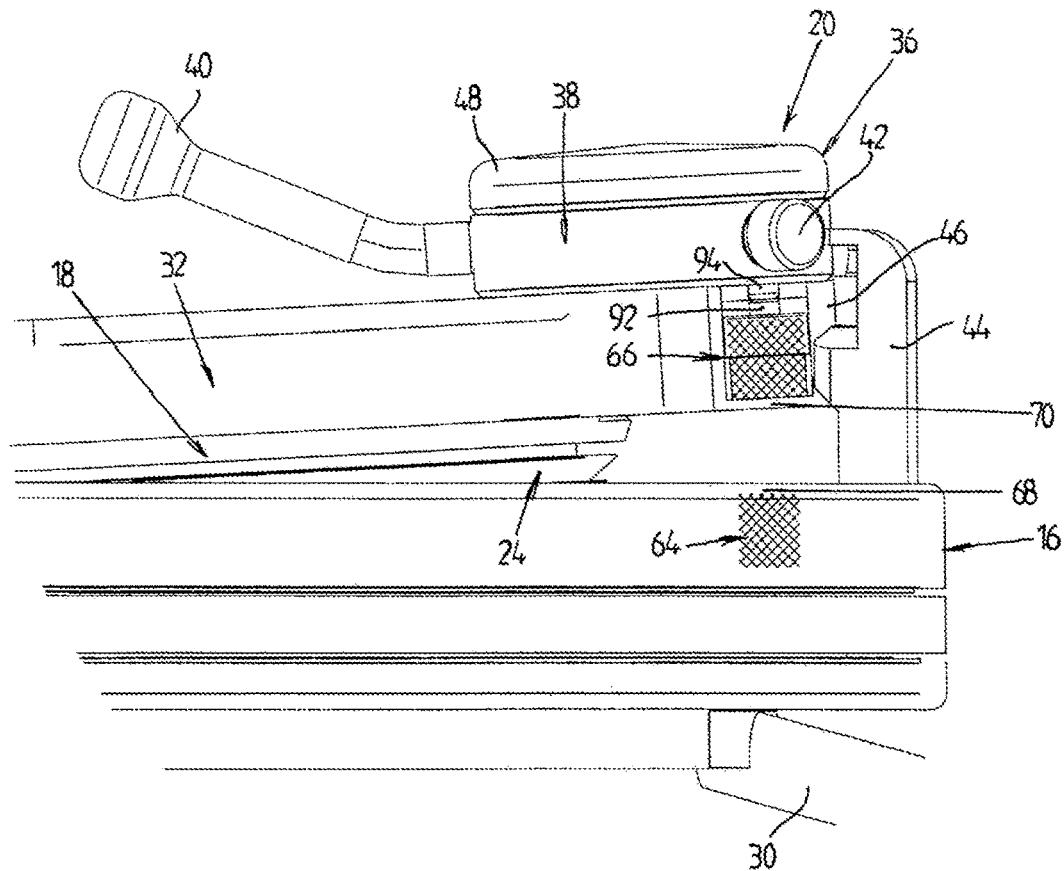
FIG. 20 is an enlarged view of the detail K of FIG. 15.

The port door 18 can be latched in its closed position via an actuation mechanism 20, which comprises a lock 36 for this purpose. The lock 36 comprises a first lock part 38, which is installed rotatably on a second projecting end of the bar 32, and which can be rotated via an actuating handle 40 between a closed position (FIG. 3) and an open position (FIG. 4), and which has a radially projecting latching tab 42. The lock 36 further comprises a second lock part 44, which is rigidly installed on the inside of the port flange 16 opposite the first lock part 38, and which has a latch receptacle 46 (FIG. 20) in which the latching tab 42 engages in the closed position to keep the port door 18 closed. The latching tab 42 is disengaged from the latch receptacle 46 in the open position.

The rotatable first lock part 38 possesses a disc-like shape and has a rigid axis (not visible) extending therethrough which projects vertically above the bar 32. A disc-like covering 48, which rotates together with the first lock part 38, is snap-fastened on to the first lock part 38.

The apparatus 10 comprises four safety devices 50, 52, 54 arranged in the alpha part 12 which are intended to prevent an improper operation of the rapid transfer port which could cause contamination of the material by unintentional contact with the environment, or contamination of the isolator by unintentional entry of germs, when material is being transferred.

The first safety device here prevents the port door 18 from opening if the container is not provided with a container cover 24, and therefore the inside of the container is not sterile. The second safety device 50 prevents the rotatable first lock part 38 from moving to the open position, and thus the port door 18 from opening, as long as the container flange 22 is not properly docked to the port flange 12. The third safety device 52 locks the container flange 22 that is properly connected to the port flange 12, and prevents the associated bayonet connection from being released as soon as the rotatable first lock part 38 leaves the closed position and heads towards the open position. The fourth safety device 54 prevents the first lock part 38 from rotating back to the closed position with the port door 18 open, and thus also prevents the unlocking of the second and third safety devices 50, 52.

To avoid the sterility of the rapid transfer port from being compromised by the safety devices 50, 52, 54, and the possibility of germs penetrating the sterile barrier of the alpha part 12, the three safety devices 50, 52, 54 each comprise two magnetic elements 56, 58; 60, 62; 64, 66, which are movable relative to one another, wherein two closed walls 68, 70 without a through-opening are arranged between the two magnetic elements 56, 58; 60, 62; 64, 66, and wherein the magnetic elements 56, 58; 60, 62; 64, 66 mutually attract or repel through the closed walls 68, 70 either in a lock position or in an unlock position of the relevant safety device 50, 52, 54.

In all three safety devices 50, 52, 54, one 56; 60; 64 of the two magnetic elements 56, 58; 60, 62; 64, 66, referred to below as the first magnetic element, is accommodated in the port flange 16, while the other one 58; 62; 66 of the two magnetic elements, referred to below as the second magnetic element, is accommodated in the bar 32 of the port door 18. The two magnetic elements 56, 58; 60, 62; 64, 66 each comprise a cylindrical or annular magnetic body composed of a permanent-magnetic material, for example, a neodymium-iron-boron alloy or another rare earth alloy. The two magnetic bodies are each installed so that two planar end faces of the magnetic bodies are opposite one another.

The first safety device, which serves to check for the presence of the container cover 24, requires only a statically loaded seal in the port door 18 in the rapid transfer port described here, in contrast to the rapid transfer port from U.S. Pat. No. 9,704,607 B2. For this reason, and to avoid the need for every container cover to be fitted with a magnetic element, it is here configured without magnetic elements and will not be described in greater detail. The above-mentioned second, third and fourth safety devices 50, 52, 54, on the other hand, each comprise two magnetic elements 56, 58; 60, 62; 64, 66.

Figure 6:
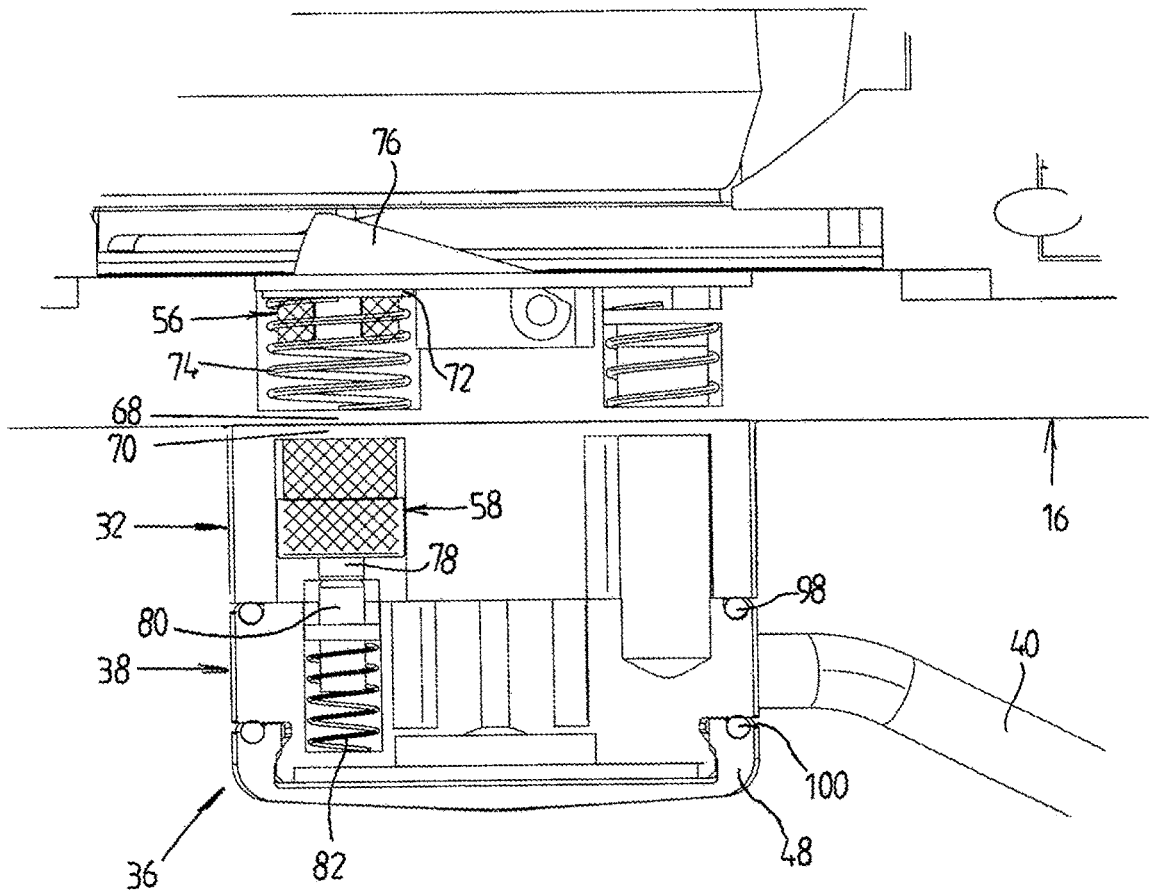
FIG. 6 is an enlarged view of the detail B of FIG. 5.
Figure 7:
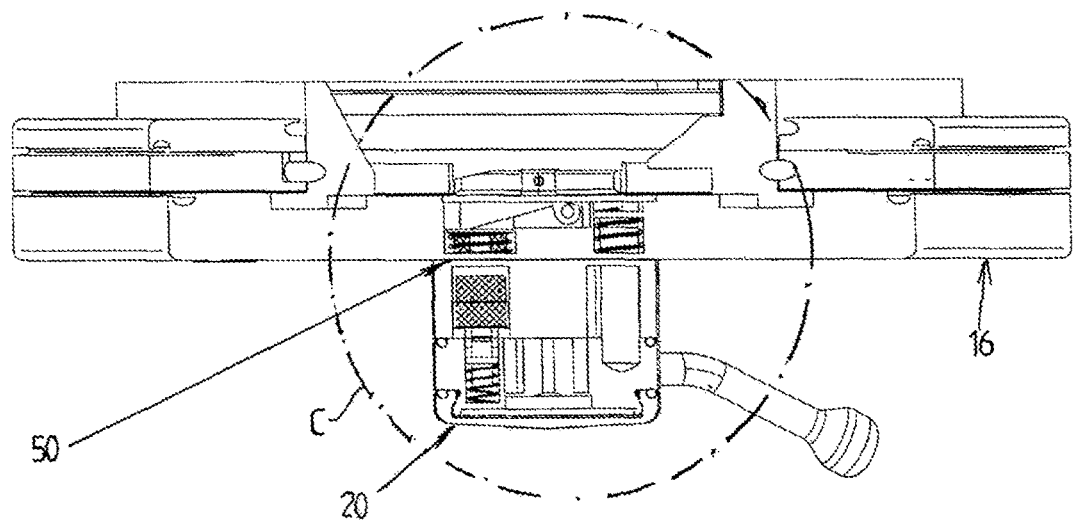
FIG. 7 is a sectional view along the line A-A of FIG. 3 after the docking of the container and in the closed state of the lock.
Figure 8:
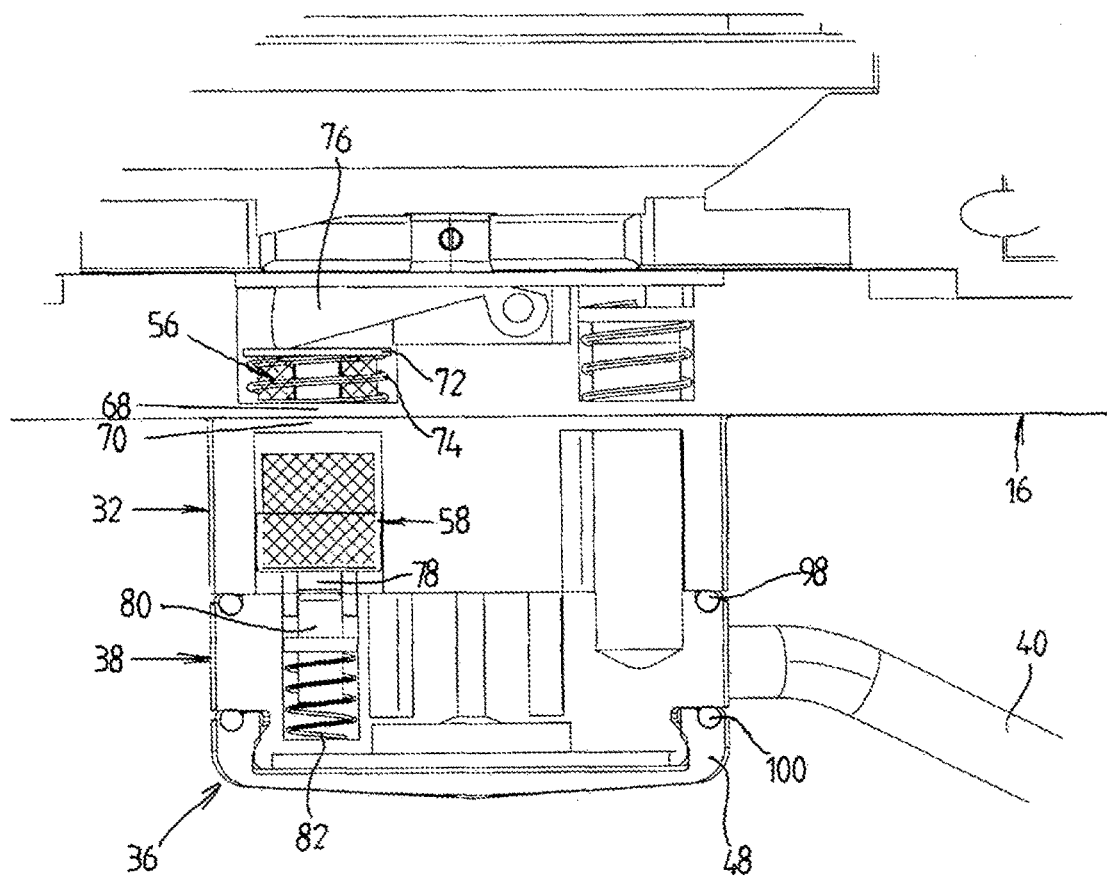
FIG. 8 is an enlarged view of the detail C of FIG. 7.
Figure 9:
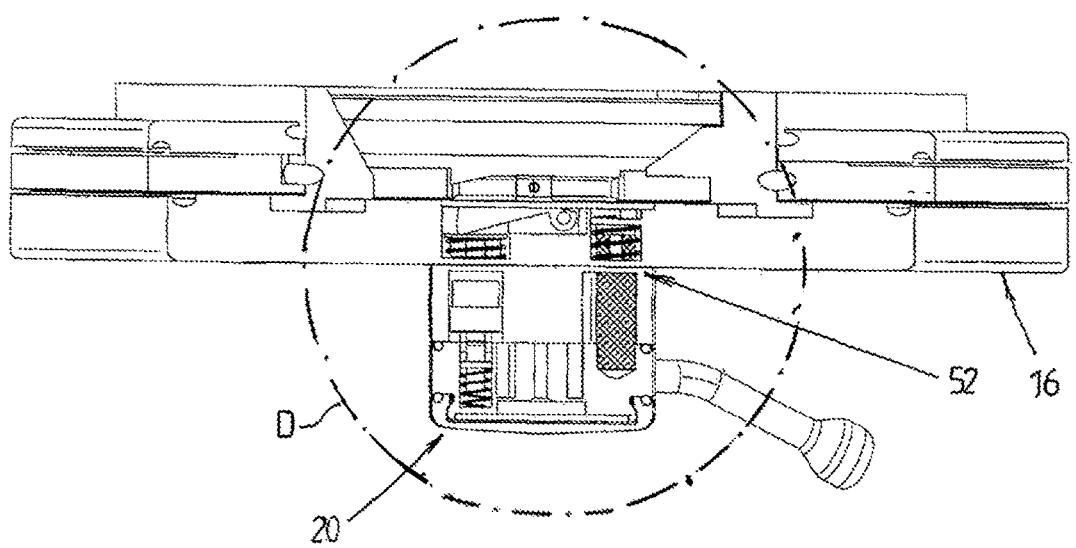
FIG. 9 is a further sectional view along the line A-A of FIG. 3 after the docking of the container and in the closed state of the lock.
Figure 13:
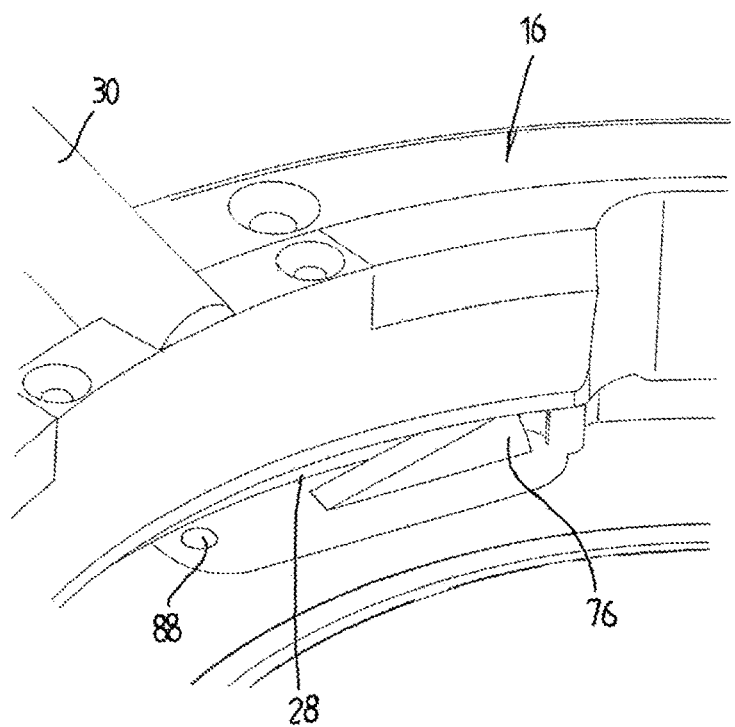
FIG. 13 is an enlarged view of the detail G of FIG. 1 in a state before the docking of the container.
Figure 14:
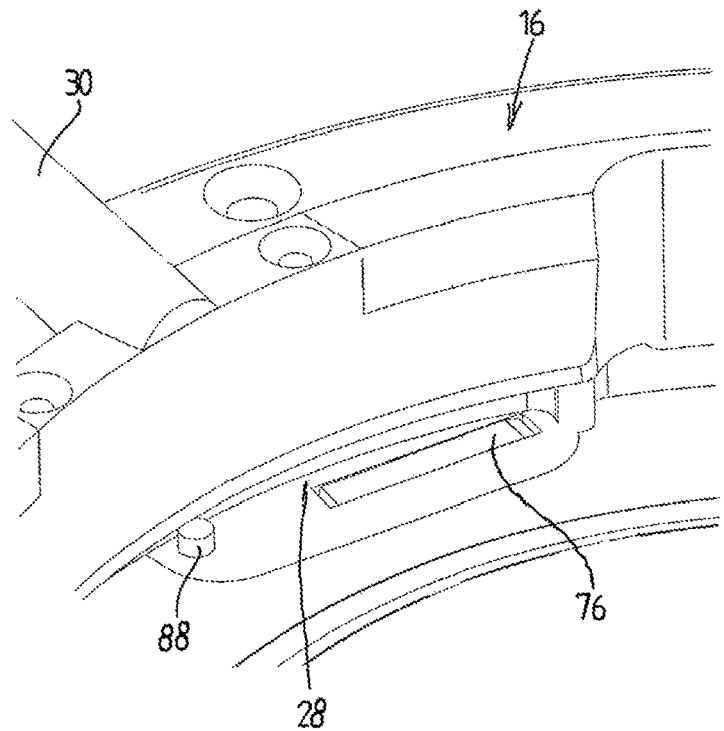
FIG. 14 is an enlarged view of the detail G of FIG. 1 in a state after the docking of the container (not shown in FIG. 10)
Figure 15:
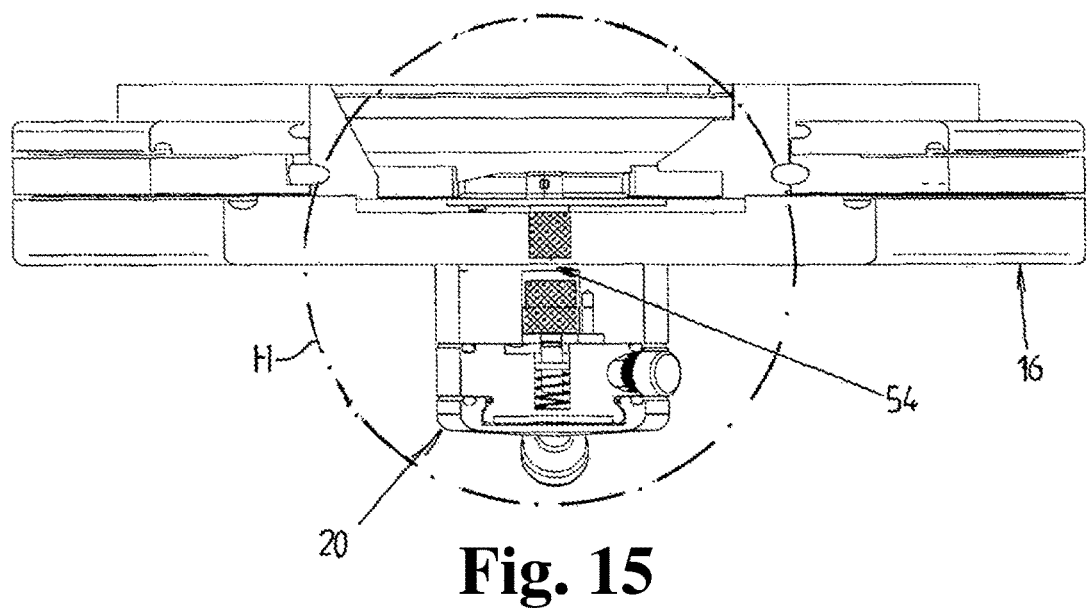
FIG. 15 is a sectional view along the line E-E of FIG. 4 after the docking of the container, in the open state of the lock and before the opening of the port door.

As best illustrated in FIGS. 5-8, 13 and 14, in the second safety device 50, the first magnetic element 56 installed in the port flange 16 consists of an annular magnetic body and a mount 72, which are movable against the force of a return spring 74 in a blind hole of the port flange 16. The mount 72 comprises a plate and a pin, which passes through the annular magnetic body. A catch 76 mounted pivotably in the port flange 16 close to the blind hole acts on the plate. The catch 76 protrudes into the receiving groove 28 of the port flange 16 before the docking of the container, as illustrated in FIG. 13, and if the two flanges 16, 22 are properly connected to each other with the lugs 26 abutting against a stop of the port flange 16, it is completely depressed there by one of the lugs 26 of the container flange 22, as illustrated in FIG. 14. After the undocking of the container, the catch 76 is moved back into the receiving groove 28 by the return spring 74, as illustrated in FIG. 13. According to the pivot position of the catch 76, the first magnetic element 56 is moved back and forth between two end positions, as illustrated in FIGS. 6 and 8. When the catch 76 protrudes into the receiving groove 28, the first magnetic element 56 is in the first end position (FIG. 6), whereas it is in the second end position at the bottom of the blind hole (FIG. 8) when the catch 76 is depressed. The blind hole is closed off from the bar 32 by the closed wall 68, which consists of thin, stainless and non-magnetic sheet steel.

The second magnetic element 58 is located inside the bar 32 opposite the first magnetic element 56. Besides a cylindrical magnetic body, the second magnetic element 58 comprises a pin 78, which projects beyond the side of the magnetic body facing away from the port flange 16. The magnetic body and the pin 78 are movable in a blind hole of the bar 32, which is closed off from the port flange by the closed wall 70. The closed wall 70 likewise consists of thin, stainless and non-magnetic sheet steel.

As best illustrated in FIGS. 6 and 8, the pin 78 abuts, with its end face that faces away from the magnetic body, against a further pin 80, which is mounted in a hole of the rotatable first lock part 38 so as to be axially slidable against the force of a return spring 82. The return spring 82 presses the second magnetic element 58 against the closed wall 70 via the pins 80, 78 when the first magnetic element 56 is in its first end position with the catch 76 unloaded.

The two magnetic bodies are oriented so that they mutually repel. When the catch 76 is depressed and the first magnetic element 56 is thereby moved to the second end position and brought closer to the second magnetic element 58, the second magnetic element 58 is lifted from the bottom of the blind hole against the force of the return spring 82. The repulsive forces of the two magnetic elements 56, 58 are adjusted to the spring force of the return spring 82 so that the abutting planar end faces of the two pins 78, 80 are flush with a planar contact surface of the rotatable first lock part 38 on the bar 32 when the catch 76 is fully depressed. This position, illustrated in FIG. 8, is the unlock position of the second safety device 50, in which the rotatable lock part 38 can be rotated from the closed position of the lock 36 to the open position thereof.

When the catch 76 moves back to the position illustrated in FIGS. 6 and 13 when the container is undocked, the second safety device 50 assumes the lock position, in which the rotatable first lock part 38 cannot be moved out of the closed position.

As best illustrated in FIGS. 9-12, in the third safety device 52, the first magnetic element 60 installed in the port flange 16 has a configuration corresponding to that of the second safety device 50 and consists of an annular magnetic body and a mount 84, which are movable against the force of a return spring 86 in a blind hole of the port flange 16. The mount 84 consists of a plate and two pins, one of which passes through the annular magnetic body. The other pin projects beyond the opposite side of the plate. The magnetic body and the two pins are axially movable in the blind hole, which towards the bar 32 is closed by the closed wall 68.

Figure 3:
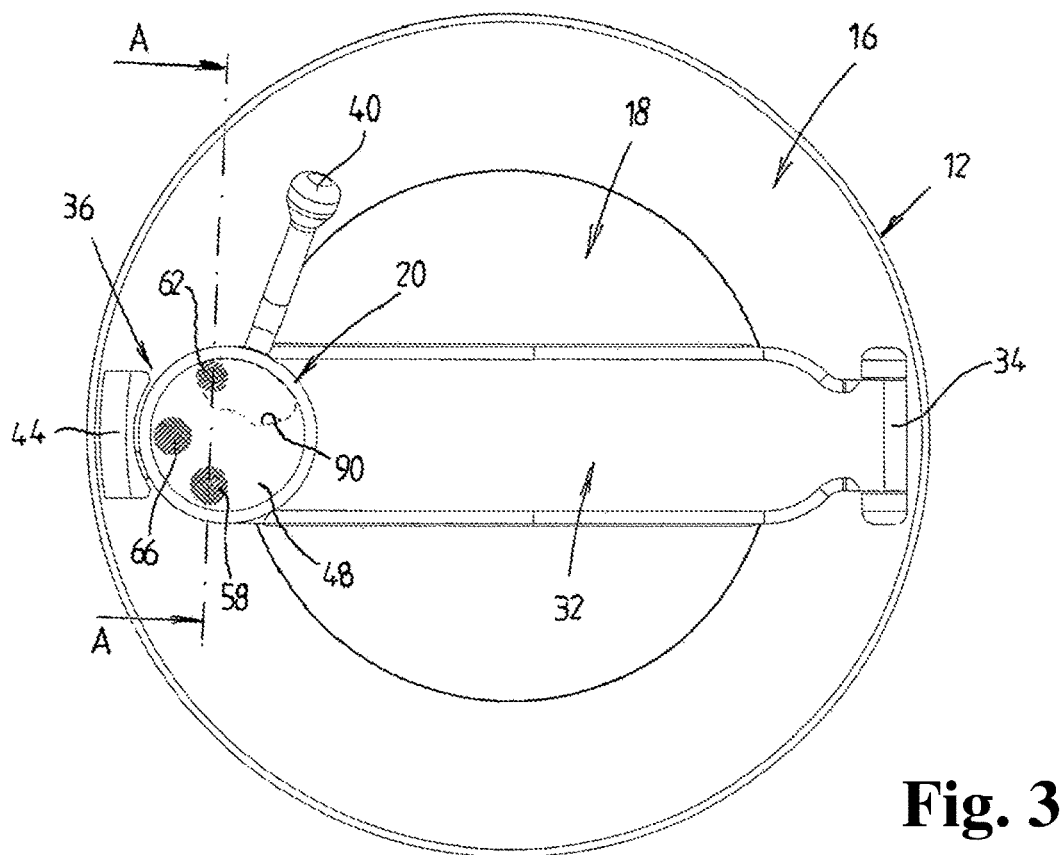
FIG. 3 is a top view of the opposite side of the port flange and the port door before the opening of a lock of the actuation mechanism.
Figure 4:
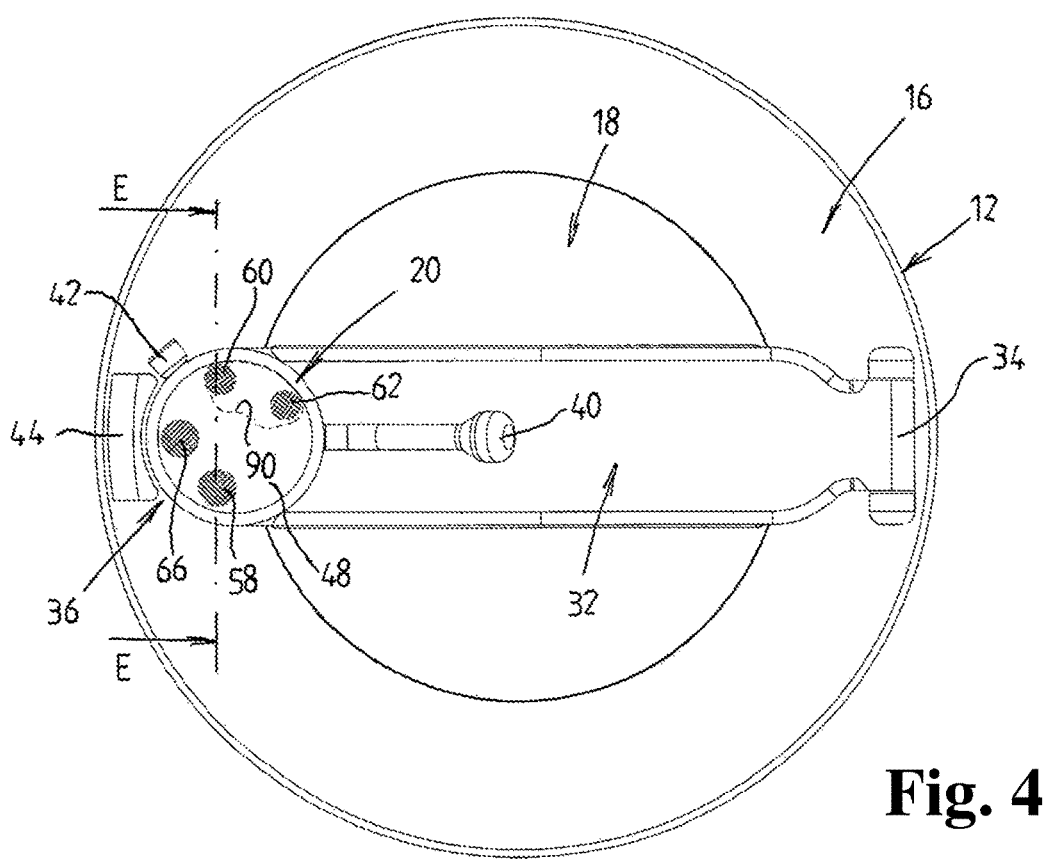
FIG. 4 is a view corresponding to FIG. 3, but after the opening of the lock.
Figure 5:
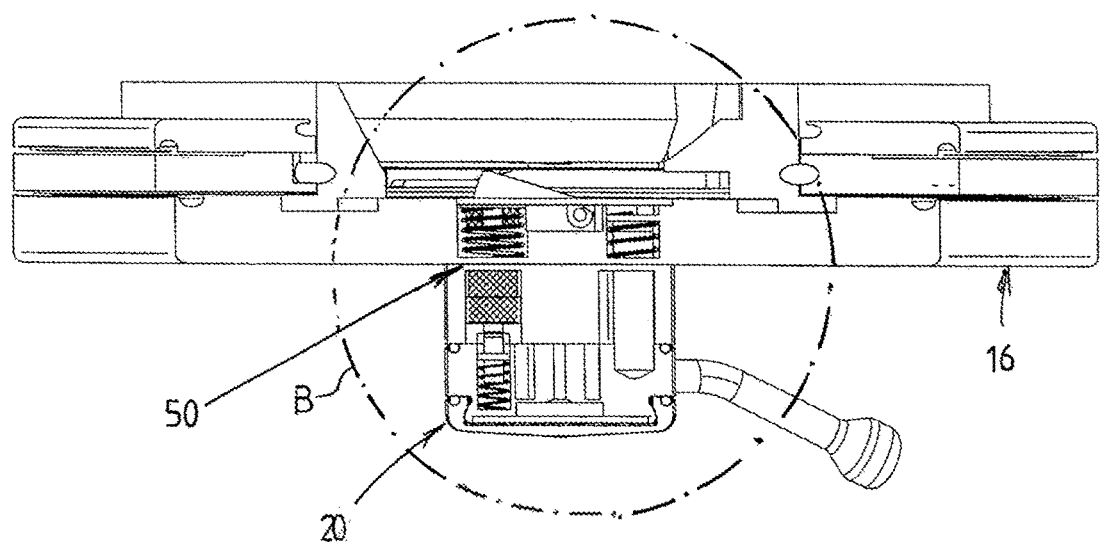
FIG. 5 is a sectional view along the line A-A of FIG. 3 before the docking of the container and in the closed state of the lock.
Figure 10:
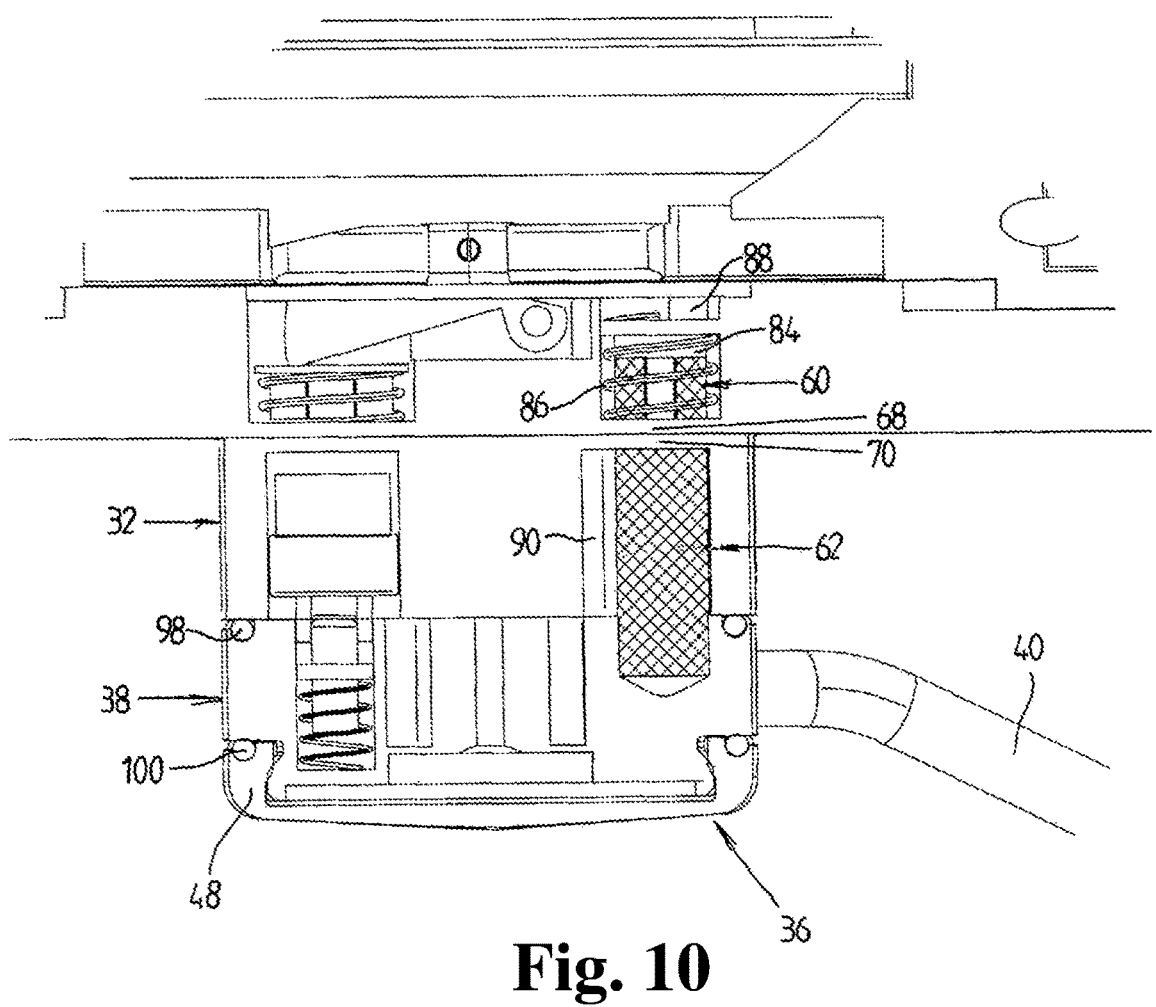
FIG. 10 is an enlarged view of the detail D of FIG. 9.
Figure 11:
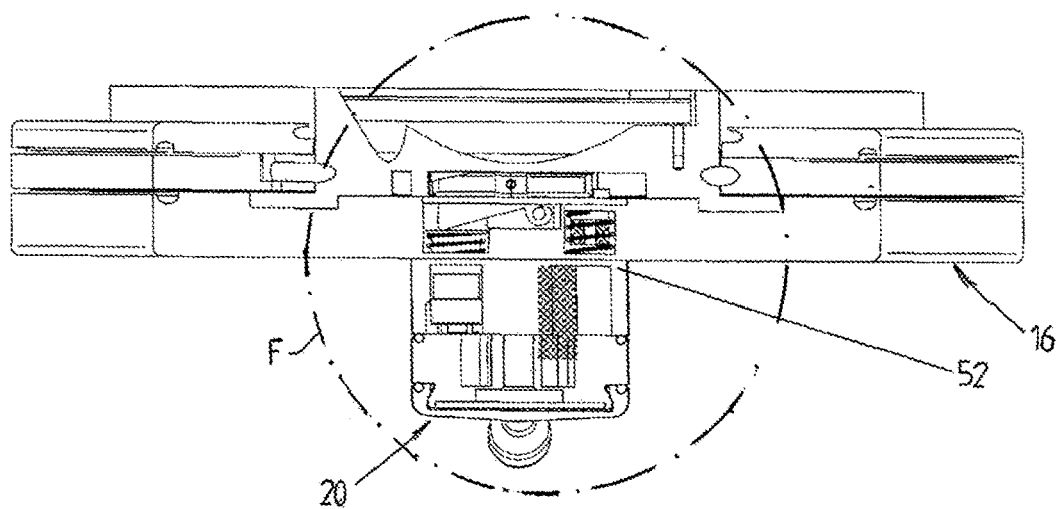
FIG. 11 is a sectional view along the line E-E of FIG. 4 after the docking of the container, in the open state of the lock and before the opening of the port door.
Figure 12:
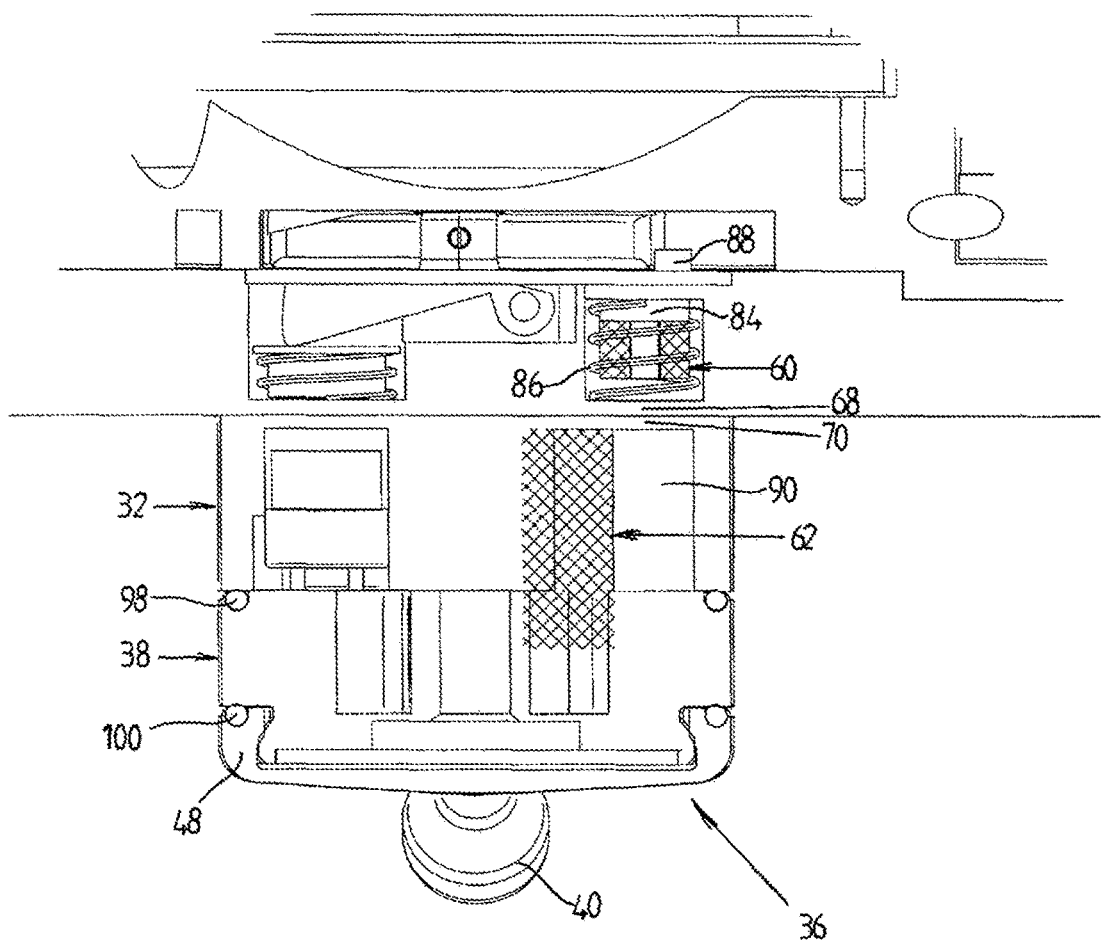
FIG. 12 is an enlarged view of the detail F of FIG. 11.

The second magnetic element 62 consists of a long cylindrical magnetic body, which is co-rotatably connected to the rotatable first lock part 38, projects beyond the side of the first lock part 38 facing the port flange 16, and protrudes into a curved elongated hole 90 of the bar 32, which is closed off at the bottom from the port flange 16 by the closed wall 70. When the rotatable first lock part 38 is in its closed position, as illustrated in FIGS. 3 and 10, the second magnetic element 62 is arranged exactly opposite the first magnetic element 60. When the rotatable first lock part 38 is in its open position, as illustrated in FIGS. 4 and 12, the second magnetic element 62 is laterally shifted relative to the first magnetic element 60.

The two magnetic bodies are oriented so that they mutually attract when the second magnetic element 62 is opposite the first magnetic element 60 in the closed position of the lock 36. The attractive forces of the two magnetic elements 60, 62 are adjusted to the spring force of the return spring 86 so that, in this unlock position of the third safety device 52, the first magnetic element 60 assumes a first end position in which the pin 88 is pulled back completely from the receiving groove 28 against the force of the return spring 86 (FIG. 13). When the second magnetic element 62 is moved away from the first magnetic element 60 in the direction of rotation within the elongated hole 90 upon rotation of the first lock part 38 to the open position, the magnetic attractive forces between the magnetic elements 60, 62 diminish to such an extent that the first magnetic element 60 is pressed back by the return spring 86 to the second end position, in which the pin 88 again protrudes into the receiving groove 28 (FIG. 14) and the third safety device 52 is in its lock position. The position of the pin 88 in the receiving groove 28 is selected so that it protrudes into the receiving groove 28 immediately behind one of the lugs 26 of the container flange 22 and prevents the lug 26 or the container flange 22 from rotating back.

Figure 16:
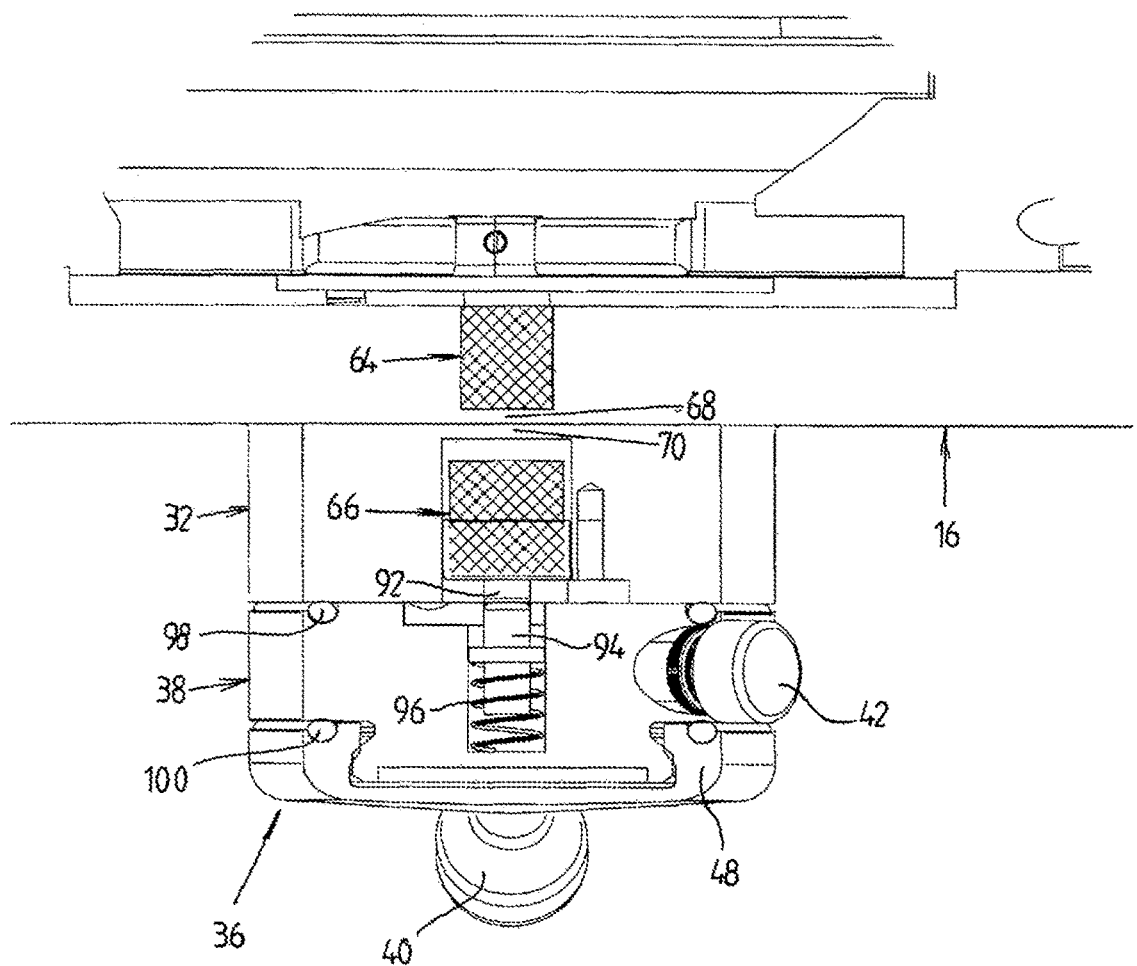
FIG. 16 is an enlarged view of the detail H of FIG. 15.
Figure 17:
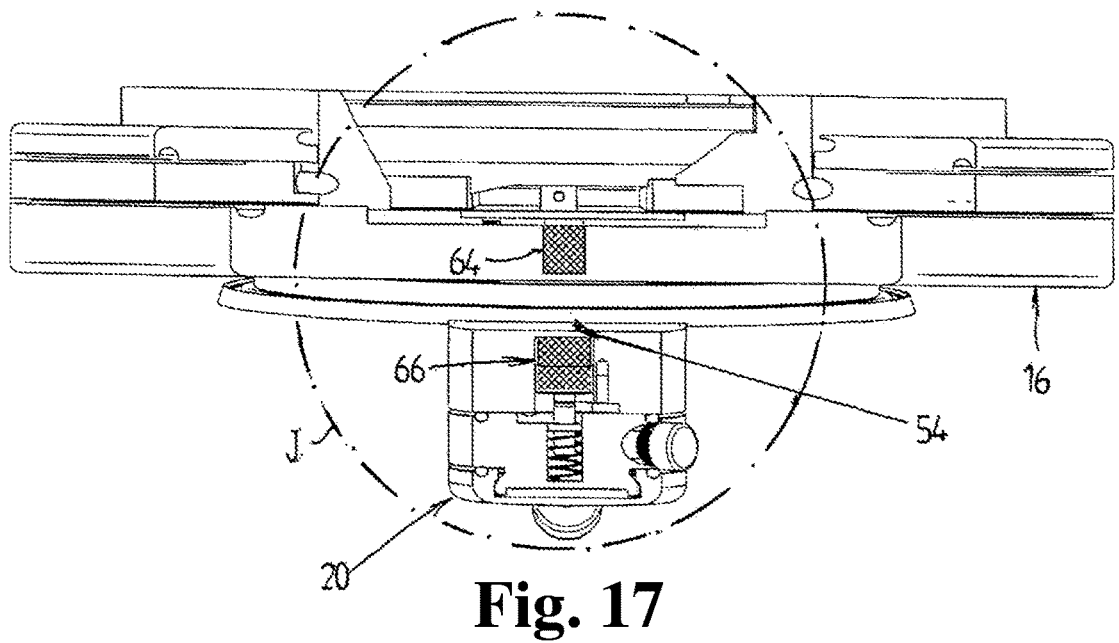
FIG. 17 is a perspective sectional view along the line E-E of FIG. 4 after the docking of the container, in the open state of the lock and with a slightly open port door.
Figure 18:
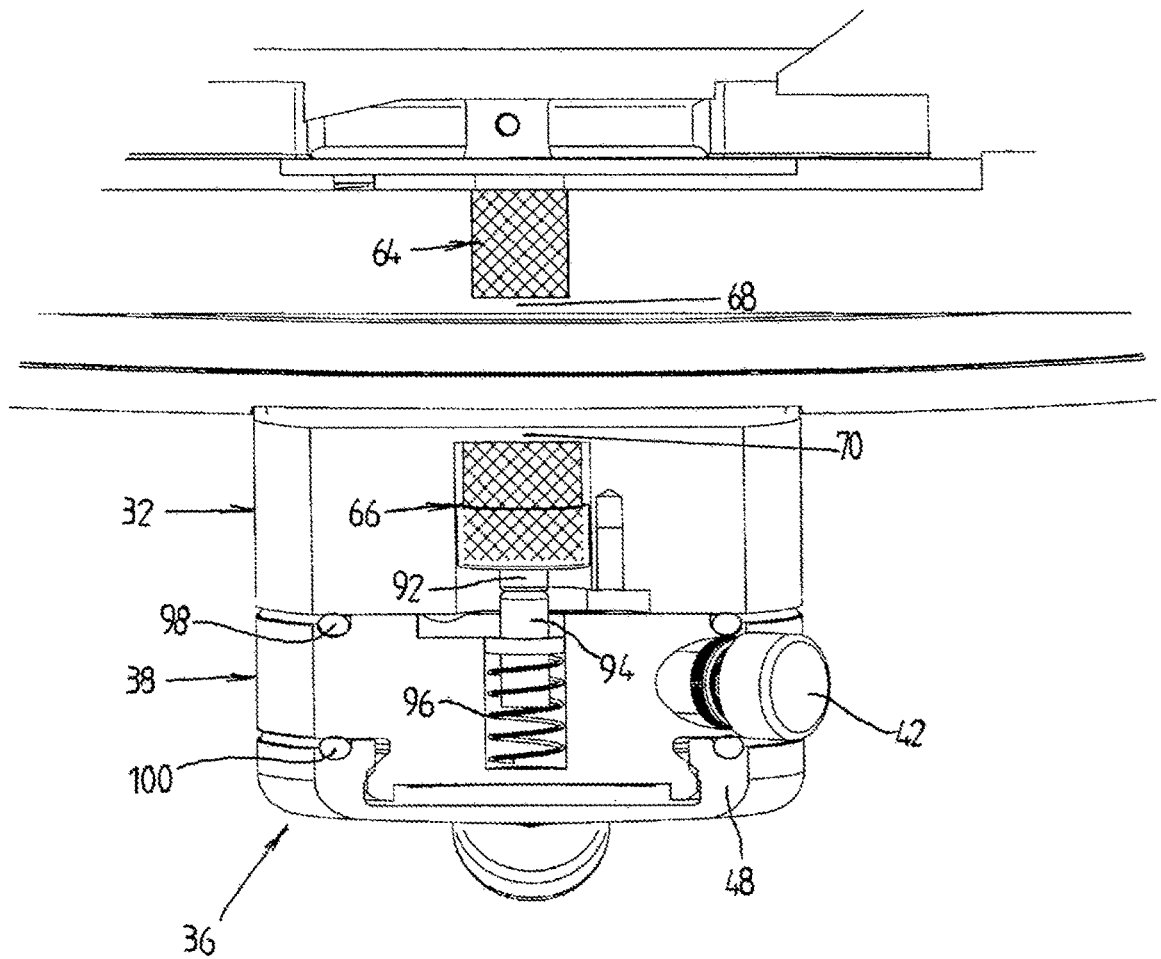
FIG. 18 is an enlarged view of the detail I of FIG. 17.
Figure 19:
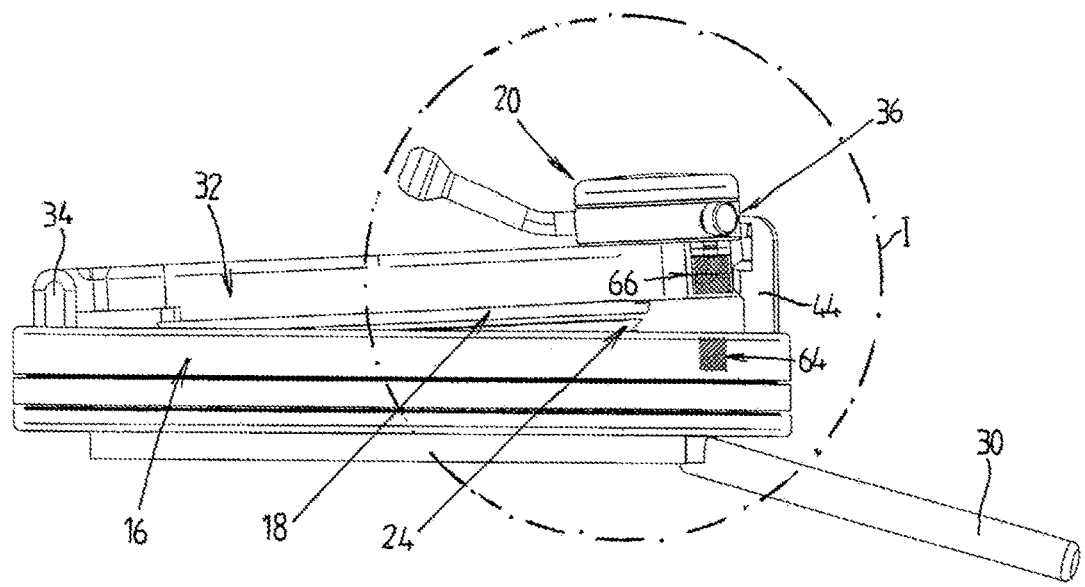
FIG. 19 is a partially sectional side view of the port flange and the port door after the opening of the lock and with a slightly open port door.

As best illustrated in FIGS. 15-20, in the fourth safety device 54, the first magnetic element 64 consists only of a fixed magnetic body installed in the port flange 16, which magnetic body is separated from the inside of the isolator by the closed wall 68 on the inside of the port flange 16. The second magnetic element 66 is located directly opposite the first magnetic element 64 inside the bar 32, so that when the port door 18 is opened, it moves with the port door 18 away from the first magnetic element 64, and when the port door 18 is closed, it moves with the port door 18 closer to the first magnetic element 64. Besides the magnetic body, the second magnetic element 66 comprises a pin 92 which projects beyond the side of the magnetic body facing away from the port flange 16. The magnetic body and the pin 92 are axially movable in a blind hole of the bar 32, which is closed off from the port flange 16 by the closed wall 70. As best illustrated in FIGS. 16 and 18, the pin 92 abuts, with its planar end face that faces away from the magnetic body, against the planar end face of a further pin 94, which is mounted in a blind hole of the rotatable first lock part 38 so as to be axially slidable against the force of a return spring 96.

The two magnetic bodies are oriented so that they mutually repel when the port door 18 is closed and the second magnetic element 66 is thus brought closer to the first magnetic element 64. The repulsive forces of the two magnetic elements 64, 66 are adjusted to the spring force of the return spring 96 so that the abutting planar end faces of the two pins 92, 94 are flush with the planar contact surface of the rotatable first lock part 38 on the bar 32 when the bar 32 abuts against the port flange 16 with the port door 18 closed. This position is the unlock position of the fourth safety device 54, in which the rotatable first lock part 38 can be rotated back from the open position of the lock 36 to the closed position.

When the port door 18 is opened slightly in the open position of the lock 36, the repulsive forces between the two magnetic elements 64, 66 diminish. The force of the return spring 96 thereby moves the second magnetic element 66 towards the closed wall 70 within the hole, causing the abutting planar end faces of the two pins 92, 94 to move out of the plane of the contact surface of the rotatable first lock part 38 on the bar 32, as best illustrated in FIG. 18. In this lock position of the fourth safety device 54, the rotatable first lock part 38 cannot be rotated out of the open position of the lock 36 to its closed position.

As best illustrated in FIGS. 6, 8, 10, 12, 16 and 18, the rotatable first lock part 38 is sealed off from both the bar 32 and the covering 48 by O-rings 98, 100, which extend along the outer perimeter of the rotatable first lock part 38 and the covering 48 respectively.

The present invention is not limited to embodiments described herein; reference should be had to the appended claims.

LIST OF REFERENCE NUMERALS

10 Apparatus
12 Alpha part
14 Beta part
16 Port flange
18 Port door
20 Actuation mechanism
22 Container flange
24 Container cover
26 Lug
28 Receiving groove
30 Lever
32 Bar
34 Pivot joint
36 Lock
38 First lock part
40 Actuating handle
42 Latching tab
44 Second lock part
46 Latch receptacle
48 Covering
50 Second safety device
52 Third safety device
54 Fourth safety device
56 First magnetic element
58 Second magnetic element
60 First magnetic element
62 Second magnetic element
64 First magnetic element
66 Second magnetic element
68 Closed wall
70 Closed wall
72 Mount
74 Return spring
76 Catch
78 Pin
80 Pin
82 Return spring
84 Mount
86 Return spring
88 Pin
90 Elongated hole
92 Pin
94 Pin
96 Return spring
98 O-ring
100 O-ring

What is claimed is:

1. An apparatus for a sterile transfer of a material between a container and an isolator, wherein,
the container comprises,
a container opening,
a container flange which is configured to surround the container opening, and
a container cover which is configured to close off the container opening and to be removable from the container flange, and
the isolator comprises,
a port opening,
a port flange which is configured to surround the port opening,
a port door which is configured to close off the port opening, and
an actuation mechanism which is configured to move between a closed position and an open position so as to open and close the port door,
wherein,
the container flange is configured to be releasably connected to the port flange, and
the container cover is configured to be releasably connected to the port door, the apparatus comprising at least one of,
a first safety device which is configured to lock the actuation mechanism in the closed position and to unlock the actuation mechanism when the port door abuts against the container cover,
a second safety device which is configured to lock the actuation mechanism in the closed position and unlock the actuation mechanism when the container flange is correctly connected to the port flange,
a third safety device which is configured to lock the container flange connected to the port flange when the actuation mechanism leaves the closed position,
a fourth safety device which is configured to block a return of the actuation mechanism from the open position to the closed position when the port door is open, and
a fifth safety device which is configured to lock the actuation mechanism if the container flange is not correctly connected to the port flange between the unlocking of the actuation mechanism by the second safety device and the locking of the container flange by the third safety device, wherein, at least one of the second safety device, the third safety device, and the fourth safety device comprises two magnetic elements which are configured to be movable relative to each another, at least one closed wall without a through-opening is arranged between the two magnetic elements, and the two magnetic elements are configured to mutually attract or to mutually repel through the at least one closed wall either in a lock position or in an unlock position of the at least one of the second safety device, the third safety device and the fourth safety device, as the case might be.

2. The apparatus as recited in claim 1, wherein, two components of the apparatus are separated by the at least one closed wall and are movable with respect to each other, and a respective one of the two magnetic elements is arranged in each of the two components.

3. The apparatus as recited in claim 1, wherein each of the two magnetic elements comprises at least one permanent-magnetic body.

4. The apparatus as recited in claim 1, wherein, the two magnetic elements comprises a first magnetic element and a second magnetic element, the first magnetic element comprises at least one ferromagnetic body, and the second magnetic element comprises at least one permanent-magnetic body.

5. The apparatus as recited in claim 1, wherein at least one of the two magnetic elements is configured to be movable between a first end position and a second end position.

6. The apparatus as recited in claim 5, further comprising:

a return spring having a spring force, wherein, the at least one of the two magnetic elements which is configured to be movable is movable against the spring force of the return spring.

7. The apparatus as recited in claim 1, wherein, the actuation mechanism comprises a lock comprising a lock part which is configured to rotate about an axis of rotation between the closed position and the open position, and at least one of the two magnetic elements is configured to move parallel to the axis of rotation of the lock part.

8. The apparatus as recited in claim 7, wherein the at least one of the two magnetic elements which is configured to move parallel to the axis of rotation of the lock part is further configured to block a rotation of the lock part in the lock position of the lock and to allow the rotation of the lock part in the unlock position.

9. The apparatus as recited in claim 1, wherein, the actuation mechanism comprises a lock comprising a lock part which is configured to rotate about an axis of rotation between the closed position and the open position, and one of the two magnetic elements is configured to rotate about the axis of rotation together with the lock part.

10. The apparatus as recited in claim 1, wherein the two magnetic elements each comprise a first magnetic element which is arranged in the port flange.

11. The apparatus as recited in claim 10, wherein the first magnetic element is configured to move in the port flange.

12. The apparatus as recited in claim 10, wherein the two magnetic elements of the second safety device further comprise a second magnetic element which is configured to unlock the actuation mechanism in the closed position when the first magnetic element is brought closer to the second magnetic element upon the connection of the container flange to the port flange.

13. The apparatus as recited in claim 10, wherein the two magnetic elements of the third safety device further comprise a second magnetic element which is configured to move away from the first magnetic element when the actuation mechanism is moved into the open position, whereupon the first magnetic element locks the container flange which is connected to the port flange.

14. The apparatus as recited in claim 10, wherein the two magnetic elements of the fourth safety device further comprise a second magnetic element which is configured to move together with the port door and to lock the actuation mechanism in the open position when the second magnetic element moves away from the first magnetic element when the port door is being opened.

* * * * *